US008465426B2

(12) United States Patent
Kanai et al.

(10) Patent No.: US 8,465,426 B2
(45) Date of Patent: Jun. 18, 2013

(54) ULTRASONOGRAPH

(75) Inventors: Hiroshi Kanai, Miyagi (JP); Hideyuki Hasegawa, Miyagi (JP); Takenori Fukumoto, Kanagawa (JP)

(73) Assignees: Tohoku University, Miyagi (JP); Panasonic Corporation, Osaka (JP)

( * ) Notice: Subject to any disclaimer, the term of this patent is extended or adjusted under 35 U.S.C. 154(b) by 550 days.

(21) Appl. No.: 12/438,021

(22) PCT Filed: Aug. 15, 2007

(86) PCT No.: PCT/JP2007/065901
§ 371 (c)(1),
(2), (4) Date: Jun. 10, 2009

(87) PCT Pub. No.: WO2008/023618
PCT Pub. Date: Feb. 28, 2008

(65) Prior Publication Data
US 2010/0063391 A1    Mar. 11, 2010

(30) Foreign Application Priority Data

Aug. 21, 2006  (JP) .................................. 2006-224064

(51) Int. Cl.
*A61B 8/00* (2006.01)
*A61B 8/13* (2006.01)
(52) U.S. Cl.
USPC ............................. 600/437; 600/443; 600/449
(58) Field of Classification Search
USPC ....................................................... 600/437
See application file for complete search history.

(56) References Cited

U.S. PATENT DOCUMENTS

| 4,370,985 A | * | 2/1983 | Takeichi et al. | 600/440 |
| 4,721,113 A | * | 1/1988 | Stewart et al. | 600/449 |
| 5,785,654 A | * | 7/1998 | Iinuma et al. | 600/441 |
| 6,132,373 A | * | 10/2000 | Ito et al. | 600/437 |
| 6,267,728 B1 | * | 7/2001 | Hayden | 600/481 |

(Continued)

FOREIGN PATENT DOCUMENTS

| EP | 1 637 081 | 3/2006 |
| JP | 08-164139 | 6/1996 |

(Continued)

OTHER PUBLICATIONS

International Search Report for corresponding Application No. PCT/JP2007/065901 mailed Nov. 13, 2007.

(Continued)

*Primary Examiner* — Long V. Le
*Assistant Examiner* — Bradley Impink
(74) *Attorney, Agent, or Firm* — Renner, Otto, Boisselle & Sklar LLP (57) ABSTRACT

An ultrasonic diagnostic apparatus according to the present invention includes: a transmitting section 102 that drives an ultrasonic probe to transmit an ultrasonic wave toward a measuring region of a subject including an arterial vascular wall; a receiving section 101 that receives a reflected wave, produced by getting the ultrasonic wave reflected by the subject, at the ultrasonic probe to generate a received signal; a movement information deriving section 110 for deriving information about at least the axial movement of the arterial vascular wall based on the received signal; and a boundary locating section 109 for locating at least one of the blood flow-intima boundary, the media-adventitia boundary and the adventitia-body's connective tissue boundary of the arterial vascular wall in the measuring region based on the movement information.

9 Claims, 5 Drawing Sheets

U.S. PATENT DOCUMENTS

| | | | | |
|---|---|---|---|---|
| 6,508,768 | B1 * | 1/2003 | Hall et al. | 600/443 |
| 6,673,020 | B2 * | 1/2004 | Okada et al. | 600/454 |
| 6,817,982 | B2 * | 11/2004 | Fritz et al. | 600/443 |
| 6,835,177 | B2 * | 12/2004 | Fritz et al. | 600/443 |
| 7,569,016 | B2 * | 8/2009 | Watanabe et al. | 600/438 |
| 7,575,551 | B2 * | 8/2009 | Watanabe et al. | 600/443 |
| 7,666,141 | B2 * | 2/2010 | Kato et al. | 600/443 |
| 7,686,764 | B2 * | 3/2010 | Watanabe et al. | 600/443 |
| 2001/0031921 | A1 * | 10/2001 | Bonnefous | 600/437 |
| 2004/0260180 | A1 * | 12/2004 | Kanai et al. | 600/449 |
| 2005/0096528 | A1 * | 5/2005 | Fritz et al. | 600/407 |
| 2005/0240101 | A1 * | 10/2005 | Kato et al. | 600/437 |
| 2007/0055149 | A1 | 3/2007 | Suzuki et al. | |
| 2007/0149877 | A1 * | 6/2007 | Oshiki et al. | 600/427 |
| 2008/0125651 | A1 | 5/2008 | Watanabe et al. | |
| 2009/0012399 | A1 * | 1/2009 | Sunagawa et al. | 600/454 |

FOREIGN PATENT DOCUMENTS

| | | |
|---|---|---|
| JP | 10-005226 | 1/1998 |
| WO | 2004/103185 | 12/2004 |
| WO | 2005/002446 | 1/2005 |
| WO | WO 2005002446 A1 * | 1/2005 |
| WO | WO 2006082966 A1 * | 8/2006 |

OTHER PUBLICATIONS

Hiroshi Furuhata, "Carotid Echo", Vector Core, Inc., 2004, ISBN 4-938372-88-6, pp. 74-83 and partial English translation (cited in [0003], p. 2 of the specification).

Spyretta Golemati et al., "Carotid Artery Wall Motion Estimated From B-Mode Ultrasound Using Region Tracking and Block Matching", Ultrasound in Med. & Biol., vol. 29, No. 3, 2003, pp. 387-399 (cited in [0025], p. 13 of the description).

Jon Bang et al., "A New Method for Analysis of Motion of Carotid Plaques from RF Ultrasound Images", Ultrasound in Med. & Biol., vol. 29, No. 7, 2003, pp. 967-976 (cited in [0025], p. 13 of the description).

Magnus Cinthio et al., "Evaluation of an Ultrasonic Echo-Tracking Method for Measurements of Arterial Wall Movements in Two Dimensions", IEEE Transactions on Ultrasonics, Ferroelectrics and Frequency Control, vol. 52, No. 8, 2005, pp. 1300-1311 (cited in [0025], p. 13 of the description).

Takanori Numata et al., "Investigation on Interpolation Method of Ultrasonic RF Echoes for Measuring Longitudinal Displacement of Arterial Wall", The Institute of Electronics, Information and Communication Engineers, vol. 105, No. 313, 2005, pp. 43-47.

* cited by examiner

ULTRASONOGRAPH

TECHNICAL FIELD

The present invention relates to an ultrasonic diagnostic apparatus for use in medical applications and more particularly relates to an ultrasonic diagnostic apparatus for measuring a vascular wall.

BACKGROUND ART

An ultrasonic diagnostic apparatus is used to monitor an internal tissue of a subject by irradiating him or her with an ultrasonic wave and analyzing the information contained in its echo signal. For example, a conventional ultrasonic diagnostic apparatus that has been used extensively converts the intensity of an echo signal into its associated pixel luminance, thereby presenting the subject's structure as a tomographic image. In this manner, the internal structure of the subject can be known. The ultrasonic diagnostic apparatus can be used to make a noninvasive checkup on an internal tissue of a subject, and therefore, is now an indispensable device at any clinical spot along with X-ray CT and MRI.

Recently, the number of people suffering from atherosclerosis has been on the rise and measurement of CIMT with B-mode ultrasonic has been carried out more and more often using an ultrasonic diagnostic apparatus to diagnose atherosclerosis. As the atherosclerosis advances, the vascular wall becomes increasingly thick and the blood vessel becomes narrower and narrower. That is why the atherosclerosis can be diagnosed by measuring the thickness of the vascular wall. It is known that the carotid artery has a three-layer structure consisting of intima, media and adventitia that are stacked in this order. For identifying and quantifying atherosclerosis, the combined thickness of the intima and the media at the carotid artery (or intima-media thickness, which will be abbreviated herein as "IMT") is measured and used as an index to atherosclerosis. According to Non-Patent Document No. 1, if the IMT is 1.1 mm or more, the carotid is determined to have abnormally thickened.

In the prior art, the IMT is manually measured. Specifically, the operator locates the intima, media and adventitia on a tomographic image that has been generated by the method described above, and measures the thickness with a length measuring function on the tomographic image, which is usually provided for any ultrasonic diagnostic apparatus.

Also, recently, thanks to the development of electronics technologies, the precision of measurements of ultrasonic diagnostic apparatuses could be improved by leaps and bounds. As a result, as disclosed in Patent Document No. 1, some people are attempting recently to track the movement of a subject's tissue more precisely and evaluate the strain, modulus of elasticity or any other physical (attribute) property of the subject's tissue (among other things, an arterial vascular wall) mainly by analyzing the phase of the reflected wave.

Even in calculating the modulus of elasticity of a vascular wall, the thickness of the vascular wall also needs to be measured. That is why the combined thickness of a vascular wall, including the intima, media and adventitia, is manually measured with the length measuring function on a tomographic image as described above.

Patent Document No. 1: Japanese Patent Application Laid-Open Publication No. 10-5226
Non-Patent Document No. 1: Hiroshi Furuhata, Carotid Echo, Vector Core Inc., 2004, ISBN 4-938372-88-6
Non-Patent Document No. 2: S. Golemati, et al., Ultrasonic Med. Biol. Vol. 29, pp. 387-399, 2003
Non-Patent Document No. 3: J. Bang et al., Ultrasonic Med. Biol. Vol. 29, pp. 967-976, 2003
Non-Patent Document No. 4: M. Cinthio, et al., IEEE Trans. Ultrason. Ferroelect. Freq. Contr. Vol. 52, pp. 1300-1311, 2005

DISCLOSURE OF INVENTION

Problems to be Solved by the Invention

However, when measuring the thickness or the IMT of a vascular wall on a tomographic image, the operator will follow his or her own habit of recognizing or identifying the image, thus possibly causing a variation in measured value from one operator to another.

Also, if an atheroma has been produced on the vascular wall, the inner borderline of the intima (i.e., the borderline between the blood flow and the intima) and that atheroma could be presented with similar luminances on the same image, which makes it difficult to distinguish the blood flow from the intima. Likewise, it is no less difficult to locate the borderline between the adventitia and the connective tissue of the subject's body on the image.

Furthermore, an interference wave called "speckle" is superimposed on the echo signal produced from the subject. That is why the tomographic image, generated by converting the intensity of the echo signal into the luminance of its associated pixel, is affected by the speckle. For that reason, the speckle sometimes makes it difficult to locate the boundary between the vascular wall and the respective films that form the vascular wall. As a result, it may be difficult to measure the thickness of the vascular wall or the IMT accurately enough.

In order to overcome the problems described above, the present invention has an object of providing an ultrasonic diagnostic apparatus that can measure the thickness of a vascular wall or the IMT accurately enough.

Means for Solving the Problems

An ultrasonic diagnostic apparatus according to the present invention includes: a transmitting section that drives an ultrasonic probe to transmit an ultrasonic wave toward a measuring region of a subject including an arterial vascular wall; a receiving section that receives a reflected wave, produced by getting the ultrasonic wave reflected by the subject, at the ultrasonic probe to generate a received signal; a movement information deriving section for deriving information about at least the axial movement of the arterial vascular wall based on the received signal; and a boundary locating section for locating at least one of the blood flow-intima boundary, the media-adventitia boundary and the adventitia-body's connective tissue boundary of the arterial vascular wall in the measuring region based on the movement information.

In one preferred embodiment, the movement information deriving section figures out a displacement distribution curve representing the distribution of magnitudes of axial displacements that have been measured along the radius of the arterial vascular wall. And the boundary locating section locates the at least one boundary by reference to the displacement distribution curve.

In this particular preferred embodiment, the transmitting section and the receiving section scan the measuring region with the ultrasonic wave, thereby getting the received signals, each corresponding to one frame, a number of times. And the movement information deriving section compares the respective amplitudes of the received signals between two different frames, thereby calculating the magnitude of axial displacement of each measuring point within the measuring region.

In a specific preferred embodiment, the movement information deriving section calculates the degree of correlation between information about the amplitude of the received signal representing a first frame and information about the amplitude of the received signal representing a second frame, thereby calculating the magnitude of axial displacement of each measuring point between the two frames within the measuring region.

In another preferred embodiment, the movement information deriving section computes a distribution of the axial movement information along the radius of the arterial vascular wall, and the boundary locating section locates the at least one boundary by reference to the distribution of the movement information.

In still another preferred embodiment, the boundary locating section locates the blood flow-intima boundary by finding a steep rise on the displacement distribution curve that is closest to a vascular lumen.

In yet another preferred embodiment, the boundary locating section locates the media-adventitia boundary by finding a local minimum value on the displacement distribution curve that is closest to the body's connective tissue.

In yet another preferred embodiment, the boundary locating section locates the adventitia-body's connective tissue boundary by finding a steep fall on the displacement distribution curve that is closest to the body's connective tissue.

In yet another preferred embodiment, the ultrasonic diagnostic apparatus further includes a tomographic image processing section for generating a signal representing a tomographic image of the measuring region based on the received signal. The at least one boundary is superimposed on the tomographic image.

In this particular preferred embodiment, the ultrasonic diagnostic apparatus further includes a modulus of elasticity calculating section for calculating, based on the received signal, a modulus of elasticity between measuring points within the measuring region. A two-dimensional map image of the moduli of elasticity calculated is further presented.

Effects Of The Invention

According to the present invention, at least one of the blood flow-intima boundary, media-adventitia boundary, and adventitia-body's connective tissue boundary of the artery is located based on the information about the axial movement of the artery. As a result, the thickness or IMT of the vascular wall can be obtained without causing any variation in measured value between individual operators.

DESCRIPTION OF REFERENCE NUMERALS 101 receiving section
102 transmitting section
103 probe
104 beam former section
105 quadrature detection section
106 tomographic image processing section
107 amplitude information processing section
108 phase information processing section
109 boundary locating section
110 movement information deriving section
111 modulus of elasticity calculating section
112 thickness calculating section
113 image synthesizing section
114 display section
120 user interface
121 control section

BEST MODE FOR CARRYING OUT THE INVENTION

The artery dilates and contracts in the radial direction as the amount and pressure of the blood flowing through the artery vary. As a result, the arterial wall makes a periodic radial movement in one cardiac cycle. Normally, the artery is regarded as not moving in the axial direction in which the artery runs. That is why even when the movement of the arterial wall is analyzed, its axial movement is not taken into consideration.

Recently, however, as disclosed in Non-Patent Documents Nos. 2, 3 and 4, for example, it was confirmed that the wall of the carotid artery, which is subjected to measurements to get an index indicating the degree of atherosclerosis, slightly moves in the axial direction in one cardiac cycle. Such a movement would be produced because the carotid artery is pulled as the heart contracts or dilates.

Figure 1:
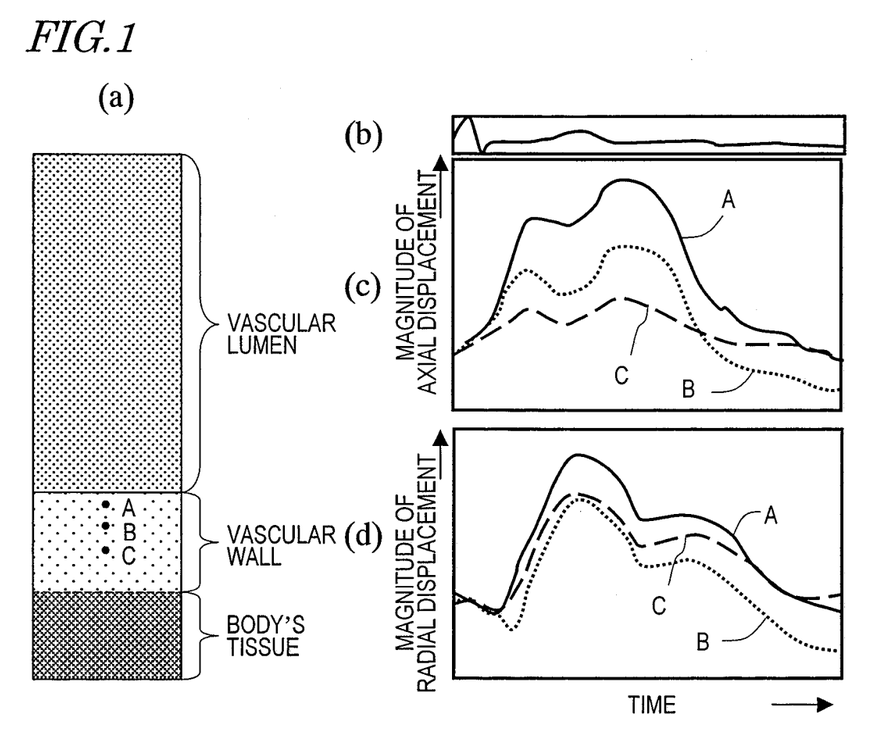
FIG. 1 illustrates the movement of a carotid arterial wall, wherein portion (a) is a schematic representation showing the measuring points that have been set on the arterial wall, portion (b) is an electrocardiographic complex of the subject, and portions (c) and (d) are graphs showing the magnitudes of axial and radial displacements of a measuring point in one cardiac cycle.

Hereinafter, the radial and axial movements of the carotid wall will be described with reference to portions (a) through (d) of FIG. 1. Specifically, portion (a) of FIG. 1 schematically illustrates the measuring region of the subject of measurements that were carried out using an ultrasonic diagnostic apparatus. As shown in portion (a) of FIG. 1, measuring points A, B and C are set in this order such that the point A is closest to the vascular lumen of the vascular wall. Portion (b) of FIG. 1 shows an electrocardiographic complex corresponding to one cardiac cycle. And portions (c) and (d) of FIG. 1 respectively show the axial displacement and the radial displacement of the measuring points A, B and C.

In portions (c) and (d) of FIG. 1, the abscissa represents the time, and displacement toward the heart and displacement toward the outside of the blood vessel are defined to be positive displacements.

As can be seen from these drawings, in a systolic phase of the heart, as the heart pumps blood and raises the blood pressure, the blood vessel dilates and the measuring points A, B and C on the vascular wall displacement toward the outside of the blood vessel. In the meantime, as the heart contracts, the vascular wall starts to move toward the heart slightly before those measuring points start to displacement on the vascular wall. And the magnitude of the movement toward the heart becomes maximum shortly after the magnitude of displacement on the vascular wall has become maximum. Also, as far as the axial displacement is concerned, the inner the measuring point on the vascular wall, the greater its magnitude of maximum displacement. In the radial direction, on the other hand, the measuring point A has the greatest magnitude of maximum displacement, while the measuring points B and C have almost the same magnitude of maximum displacement. The magnitudes of axial and radial displacements will vary in this manner with the location of the measuring point on the arterial wall because the outside of the carotid artery is covered with the connective tissue of the subject's body and because the arterial wall consists of the three different tissues of intima, media and adventitia that have mutually different moduli of elasticity.

As described above, the axial movement of the carotid wall would be produced by the contraction and dilatation of the heart. That is why if the axial movement is detected in the measuring region of the subject, including the arterial wall, then the boundaries between the vascular lumen and the body's connective tissue, which are not pulled by the heart, and the arterial wall can be located. In addition, the boundaries between the respective tissues that form the arterial wall can also be located by detecting the axial movement. Based on such an idea, the present inventors invented an ultrasonic diagnostic apparatus that can determine the thickness and IMT of a vascular wall.

Figure 2:
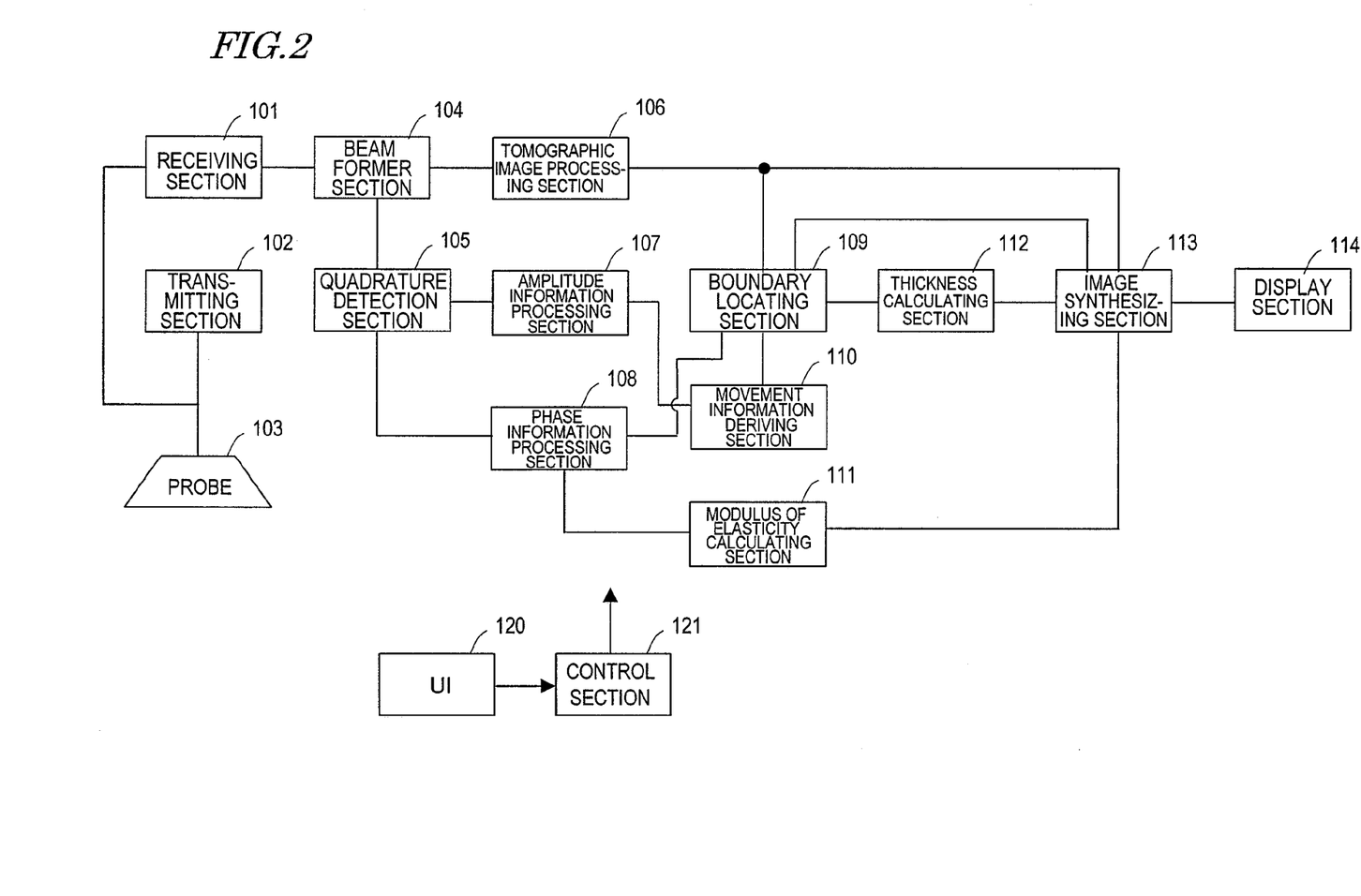
FIG. 2 is a block diagram illustrating a preferred embodiment of an ultrasonic diagnostic apparatus according to the present invention.

Hereinafter, a preferred embodiment of an ultrasonic diagnostic apparatus according to the present invention will be described in detail. FIG. 2 is a block diagram illustrating a configuration for an ultrasonic diagnostic apparatus as a preferred embodiment of the present invention. The artery, of which the boundary can be located by using the ultrasonic diagnostic apparatus of the present invention, does not have to be carotid artery but may also be any other artery as long as the artery is pulled by the heart that contracts and dilates.

The ultrasonic diagnostic apparatus of this preferred embodiment includes a receiving section 101, a transmitting section 102, a beam former section 104, an quadrature detecting section 105, a tomographic image processing section 106, an amplitude information processing section 107, a phase information processing section 108, a boundary locating section 109, a movement information deriving section 110, a modulus of elasticity calculating section 111, a thickness calculating section 112 and an image synthesizing section 113. The apparatus further includes a user interface 120 that allows the operator to enter a command into the ultrasonic diagnostic apparatus and a control section 121 (such as a microcomputer) for controlling these components in accordance with the command sent from the user interface 120.

It should be noted that not all of these components shown in FIG. 2 have to be implemented as an independent piece of hardware. For example, the phase information processing section 108, the boundary locating section 109, the movement information deriving section 110, the modulus of elasticity calculating section 111, and the thickness calculating section 112 could be implemented as a combination of a microcomputer and software programs to perform their respective functions.

To the transmitting section 102 and the receiving section 101, connected is a probe 103 that sends out an ultrasonic wave toward a subject, and receives an ultrasonic echo that has been reflected from the subject. The ultrasonic diagnostic apparatus may include a dedicated probe 103. Or a general-purpose probe could be used as the probe 103 as well. A number of piezoelectric transducers are arranged in the probe 103. By changing the piezoelectric transducers to use and the timings to apply a voltage to the piezoelectric transducers using the beam former section 104, the probe 103 controls the angle of deviation and focus of the ultrasonic waves to transmit and receive.

In accordance with the instruction given by the control section 121, the transmitting section 102 generates a high-voltage transmission signal that drives the probe 103 at a specified timing. The probe 103 converts the transmission signal that has been generated by the transmitting section 102 into an ultrasonic wave and sends the ultrasonic wave toward the subject.

The ultrasonic echo that has been reflected from the internal tissue of the subject is converted by the probe 103 into an electrical signal, which is then amplified by the receiving section 101, thereby generating a received signal. As described above, by getting the piezoelectric transducers of the probe 103 selected by the beam former section 104, the receiving section 101 can detect only an ultrasonic wave that has come from either a predetermined position (focus) or a predetermined direction (angle of deviation).

By operating the transmitting section 102, the receiving section 101 and the beam former section 104 in this manner, the measuring region of the subject is scanned with the ultrasonic wave that has been sent out from the probe 103, thereby getting a received signal for one frame. This scan operation is repeatedly performed a number of times during one cardiac cycle of the subject, thereby getting received signals for multiple frames. For example, received signals for a hundred and several tens of frames are obtained.

The tomographic image processing section 106 includes a filter, a logarithmic amplifier and a detector, and converts the received signal supplied from the receiving section 101 into a signal with luminance information representing the signal intensity. As a result, a signal representing a tomographic image in the measuring region of the subject can be obtained.

The quadrature detection section 105 subjects the received signal to an quadrature detection. The amplitude information processing section 107 figures out amplitude information based on the received signal that has been subjected to the quadrature detection and outputs it to the movement information deriving section 110.

The movement information deriving section 110 gets information about at least the axial movement of the arterial vascular wall based on the amplitude information represented by the received signal that has been subjected to the quadrature detection. As long as the axial movement information can be derived, the movement information deriving section 110 may obtain either two-dimensional movement information or three-dimensional movement information. The boundary locating section 109 locates at least one of the blood flow-intima boundary, the media-adventitia boundary and the adventitia-body's connective tissue boundary of the arterial vascular wall in the measuring region based on the movement information obtained, thereby generating the location information of the boundary that has been located in the measuring region.

If the boundary locating section 109 has located two or more of the blood flow-intima boundary, the media-adventitia boundary and the adventitia-body's connective tissue boundary of the arterial vascular wall, then the thickness calculating section 112 calculates the thickness (or distance) between those boundaries located.

The phase information processing section 108 generates the phase information of the received signal that has been subjected to the quadrature detection and outputs it to the modulus of elasticity calculating section 111. Based on the phase information, the modulus of elasticity calculating section 111 calculates the magnitude of the radial displacement of each measuring point in the measuring region. The modulus of elasticity calculating section 111 also receives information about the subject's blood pressure from an external device and calculates the modulus of elasticity between each pair of measuring points based on the thickness between the boundaries that has been provided by the thickness calculating section 112, the information about the blood pressure, and the magnitude of the radial displacement of each measuring point.

The image synthesizing section 113 receives a signal representing a tomographic image of the subject in the measuring region from the tomographic image processing section 106, the location information of the boundary located from the boundary locating section 109, and the thickness between the boundaries from the thickness calculating section 112, respectively. Then, based on the location information of the boundary, the image synthesizing section 113 generates an image signal, representing a tomographic image on which a borderline indicating the boundary located is superimposed, and outputs it to the display section 14. The image synthesizing section 113 further generates a numerical value representing the thickness between the boundaries and outputs it to the display section 114, too.

The image synthesizing section 113 further receives the moduli of elasticity between the respective measuring points, generates two-dimensional map data representing the distribution of the moduli of elasticity in the measuring region in color tones and grayscales associated with those moduli of elasticity, and then outputs the map data to the display section. In response, the display section 114 presents the data that has been provided by the image synthesizing section 113.

The user interface 120 is an input section that allows the operator to enter a command into this ultrasonic diagnostic apparatus. Specifically, the user interface 120 is an input device such as a keyboard, a trackball or a mouse. Using the user interface 120, the operator may set a region of interest (ROI) in which the modulus of elasticity needs to be calculated or may determine what boundary to be located by the boundary locating section 109 and where the thickness between the boundaries should be calculated by the thickness calculating section 112.

Hereinafter, the operations of the movement information deriving section 110 and the boundary locating section 109 will be described in detail. As described above, according to the present invention, the boundaries between the vascular lumen, the body's connective tissue and the arterial wall and the boundaries between the respective tissues that form the arterial wall are located by detecting the axial movement of the subject. For that purpose, the movement information deriving section 110 receives information about the amplitude of the received signal from the amplitude information processing section 107 and plots the distribution of the axial movement information of the subject in the radial direction of the arterial vascular wall, thereby locating the boundaries based on the distribution of the movement information obtained. In this case, the movement information may be either the velocity or the magnitude of the axial displacement.

In this preferred embodiment, the boundaries are supposed to be located based on the magnitude of the axial displacement.

Information about the axial movement of the artery can be obtained by sending out ultrasonic waves toward the subject non-parallel to the radial direction. An ordinary ultrasonic diagnostic apparatus, however, is designed to collect internal information of the subject by transmitting and receiving ultrasonic waves parallel to the radial direction. That is why it is difficult for such an apparatus to detect the axial movement components directly from the received signals. For that reason, according to this preferred embodiment, the measuring region is scanned with ultrasonic waves, thereby getting received signals, each corresponding to one frame, a number of times. And the degree of correlation between the received signals is calculated between two different frames, thereby estimating the magnitude of axial displacement of each measuring point. In this manner, a displacement distribution curve of the measuring ultrasonic beam can be obtained on an acoustic line. The boundaries between the vascular lumen, the body's connective tissue and the arterial wall and the boundaries between the respective tissues that form the arterial wall are located by reference to that displacement distribution curve.

Figure 3:
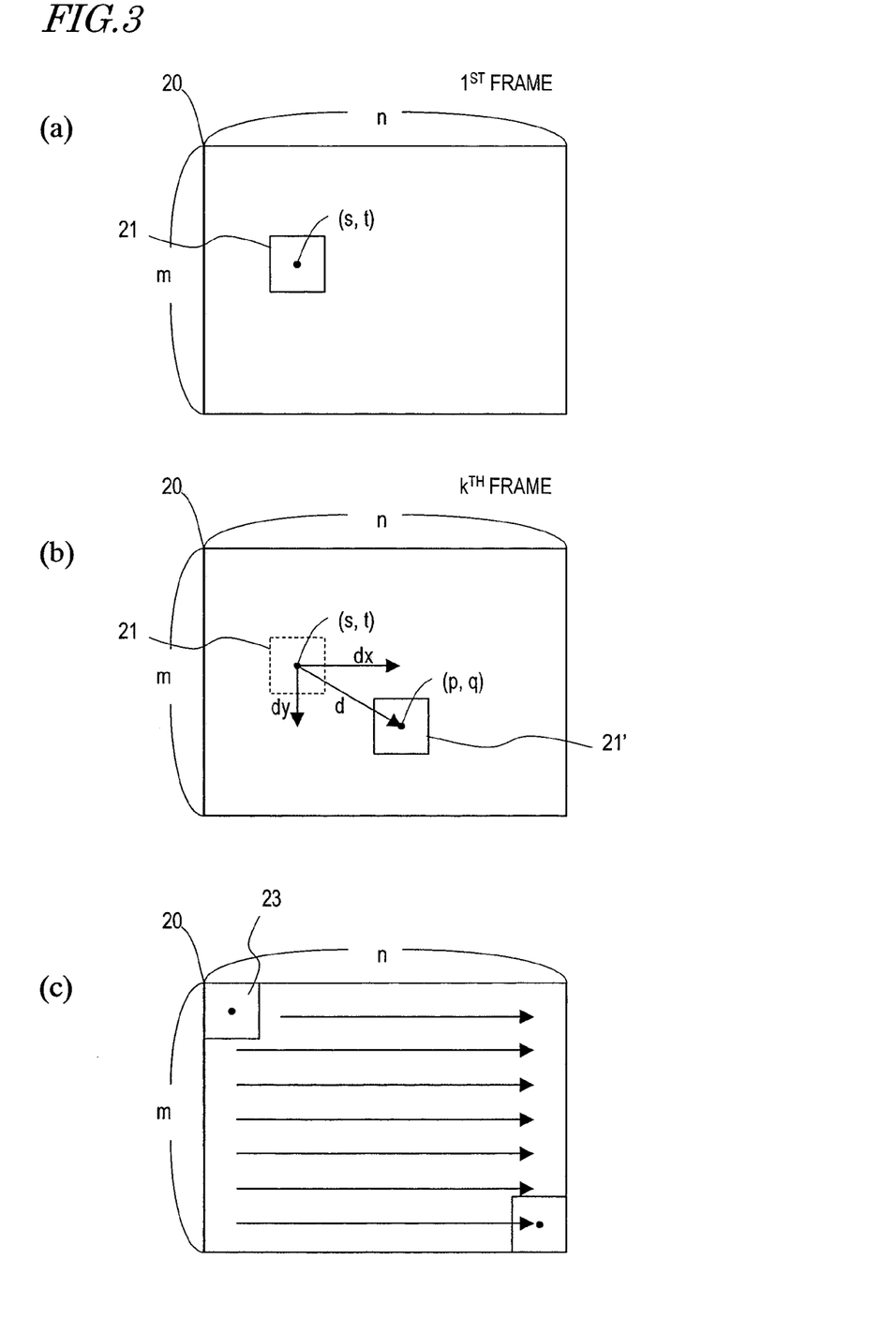
FIGS. 3(a) through 3(c) illustrate a procedure for calculating the magnitude of displacement of the arterial wall.

Hereinafter, it will be described in detail with reference to FIG. 3 exactly how to calculate the magnitude of the axial displacement. First, as shown in FIG. 3(a), a region of interest 21 to calculate the degree of correlation is set within the measuring region 20 in the first frame, for example. In this example, the measuring points are supposed to be arranged in m columns and n rows within the measuring region 20. The region of interest 21 is used to calculate the magnitude of displacement of a measuring point (s, t), where s and t are integers that are equal to or smaller than n and equal to or smaller than m, respectively.

In the $k^{th}$ frame, which is later than the first frame by a predetermined amount of time, the arterial wall is supposed to have moved by dy in the radial direction as a result of its dilatation and by dx in the axial direction as having been pulled toward the heart as shown in FIG. 3(b). In that case, the region of interest 21 that has been set has also displaced both axially and radially to be a region 21' having a measuring point (p, q) at its center. Also, in that case, a region 23 of the same size as the region of interest 21 is defined for each measuring point within the measuring region 20 as shown in FIG. 3(c) and the degree of correlation between information about the amplitude of the received signal representing the region of interest 21 in the first frame and information about the amplitude of the received signal representing the region 23 in the $k^{th}$ frame is calculated with a correlation function, thereby calculating a correlation coefficient. If the region 23 is defined for every measuring point within the measuring region 20 and if the degree of correlation is calculated, the degree of correlation between the regions 21 and 21' should be the highest and the correlation coefficient should be the greatest as shown in FIG. 3(b). That is why the region of interest 21 is estimated to have displaced and become the region 21' in the $k^{th}$ frame and the magnitude of the axial displacement becomes dx in that case. Such a method of locating a site of interest between two frames using the degree of correlation between received signals is disclosed in Japanese Patent Application Laid-Open Publication No. 8-164139, for example.

The movement information deriving section 110 makes this calculation for each measuring point, thereby calculating the magnitude of displacement of every measuring point within the measuring region between two predetermined frames. As the magnitude of axial displacement is used to locate the boundaries of the arterial vascular wall according to the present invention, the magnitude of the radial displacement does not have to be calculated.

Optionally, the degree of correlation may also be calculated with reference to the phase information that has been obtained by the phase information processing section 108. If the phase information is used, the magnitude of radial displacement of each measuring point can be obtained by comparing the phases between two frames. That is why as for the region 23 on which the degree of correlation needs to be calculated in the radial direction, the region 23 with the greatest correlation coefficient can be located by calculating the degree of correlation of either only a region 23 that has displaced radially by the magnitude of displacement that has been obtained based on the phase or only a neighboring region 23 thereof. As a result, the complexity of computation can be reduced significantly.

The precision of the correlation calculation depends on the size of the region of interest 21. Generally speaking, the bigger the region of interest, the higher the precision of calculation tends to be. But the degree of computational complexity also increases accordingly. That is why the size of the region of interest 21 is preferably determined with the complexity and required degree of precision of computation taken into account.

Figure 4:
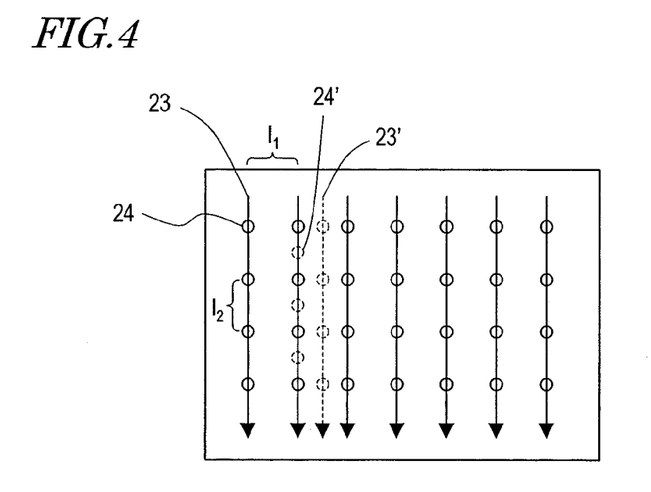
FIG. 4 shows the arrangement of measuring points in a measuring region.

According to the method described above, the axial and radial resolutions of the magnitude of displacement thus obtained are determined by the axial and radial intervals between the measuring points that have been defined in the measuring region as shown in FIG. 4. More specifically, the axial resolution is defined by the interval $I_1$ between the acoustic lines 23 of an ultrasonic beam. On the other hand, the radial resolution is defined by the interval $I_2$ between the measuring points 24 that have been set on the acoustic lines 23. If either the interval $I_1$ or $I_2$ is not broad enough to ensure sufficiently high precision of measurement of the magnitude of displacement, then an interpolated signal 23' may be generated by making an interpolation between the received signals representing two adjacent acoustic lines 23. Then, the axial resolution can be increased. Likewise, an interpolated measuring point 24' may also be generated by making an interpolation between the received signals representing two adjacent measuring points on the acoustic line 23.

Figure 5:
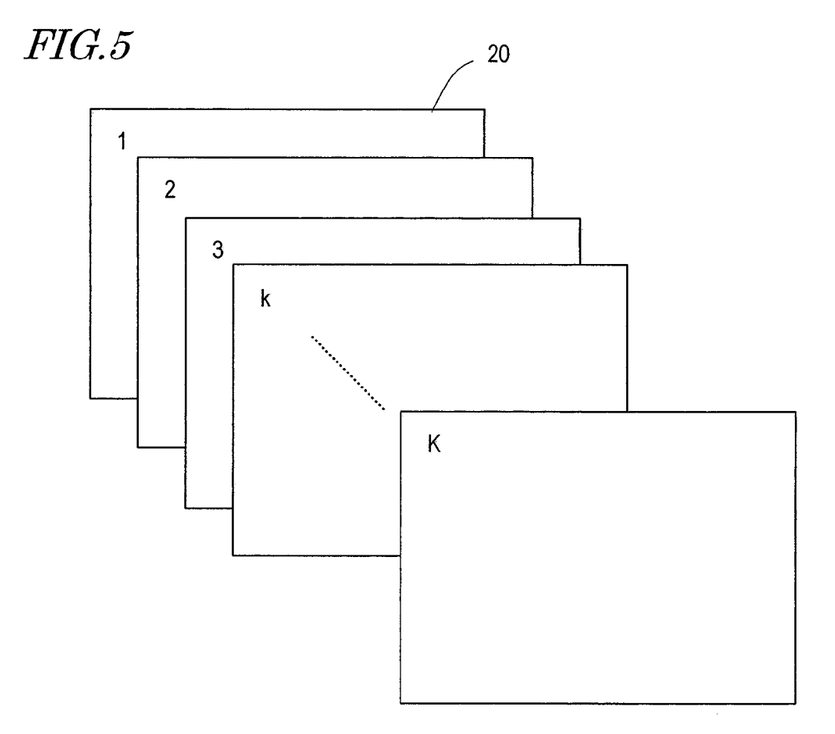
FIG. 5 shows how measurements using ultrasonic waves are carried out on a frame-by-frame basis.

As schematically shown in FIG. 5, received signals representing the measuring region 20 are obtained as the first through $k^{th}$ frames in one cardiac cycle. And by selecting two arbitrary ones of the first through $k^{th}$ frames, the magnitude of displacement of the arterial wall can be obtained between those two frames selected. Normally, by selecting a frame corresponding to a point in time when there is the smallest displacement toward the heart and a frame corresponding to a point in time when there is the greatest displacement toward the heart as shown in FIG. 1(c), the magnitude of maximum axial displacement can be obtained. As a result, the influence of noise can be reduced, and a curve representing the radial distribution of magnitudes of axial displacements (to be described later) can be plotted with high precision, thus locating the boundaries more accurately. However, as shown in FIG. 1(c), the timing of the axial movement of the arterial wall in one cardiac cycle will change according to the radial location. For that reason, frames are preferably selected such that the curve representing the radial distribution of magnitudes of axial displacements allows the user to locate the boundaries easily.

Figure 6:
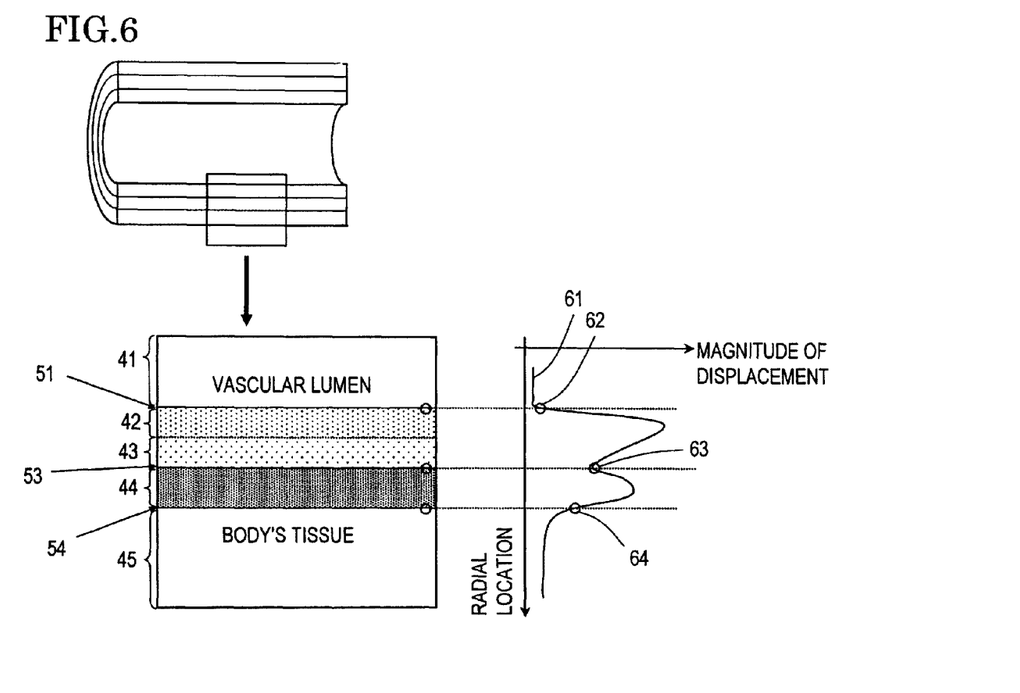
FIG. 6 shows how to locate the boundaries of the arterial wall based on a curve representing the radial distribution of the magnitudes of axial displacements.

The movement information deriving section 110 calculates the magnitudes of axial displacements of the respective measuring points along a single acoustic line (i.e., in the radial direction) by the method described above, thereby generating the displacement distribution curve. As shown in FIG. 6, by plotting the magnitudes of displacements of the respective measuring points that are arranged in the radial direction, a displacement distribution curve 61 can be obtained. FIG. 6 also illustrates schematically a tomographic image of the associated measuring region.

The boundary locating section 109 locates the boundaries of the arterial wall by reference to the displacement distribution curve that has been provided by the movement information deriving section 110. As shown in FIG. 6, on the displacement distribution curve 61 thus obtained, a steep rise point 62 that is closest to the vascular lumen 41 indicates the location of the boundary 51 between the blood flow in the vascular lumen 41 and the intima 42. On the other hand, a local minimum point 63 that is closest to the body's connective tissue 45 indicates the boundary 53 between the media 43 and the adventitia 44. And a steep fall point 64 that is closest to the body's connective tissue 45 indicates the location of the boundary 54 between the adventitia 44 and the body's connective tissue 45.

The displacement distribution curve can be associated with the boundaries of the arterial wall in this manner because neither the blood flow nor the body's connective tissue moves in the axial direction and because the respective tissues that form the arterial wall have mutually different moduli of elasticity, and therefore, have different axial movement properties.

By reference to each single displacement distribution curve, the boundary locating section 109 locates at least one of the blood flow-intima boundary, the media-adventitia boundary and the adventitia-body's connective tissue boundary in accordance with the relation described above. More specifically, with the measuring point displaced radially, the boundary locating section 209 compares the magnitude of displacement with a measuring point on the line, thereby finding the rise, local minimum and fall points on the curve as described above. The displacement distribution curve can be obtained for each acoustic line. That is why by locating the boundaries on each displacement distribution curve, the blood flow-intima boundary, the media-adventitia boundary or the adventitia-body's connective tissue boundary can be located in the entire measuring region.

Figure 7:
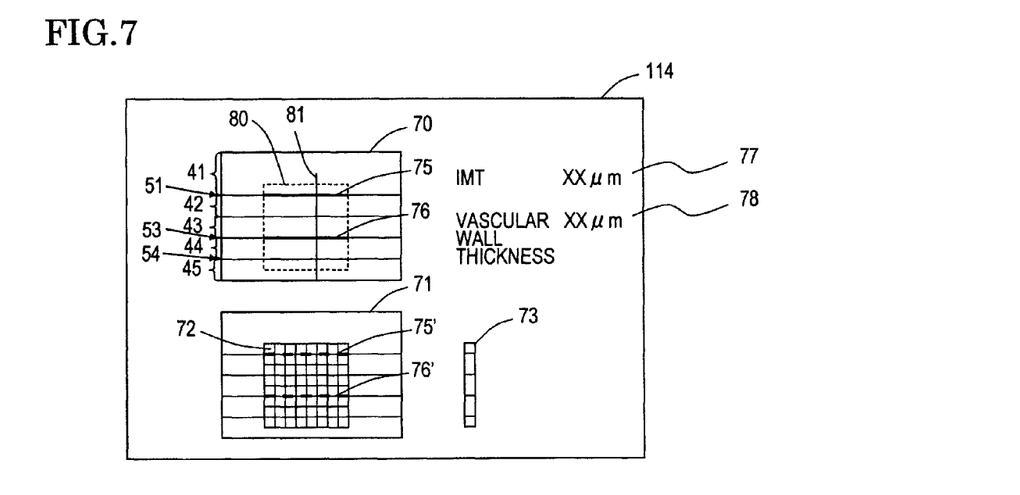
FIG. 7 illustrates an exemplary image to be presented on a display section in a situation where the subject, including the arterial wall, is inspected using the ultrasonic diagnostic apparatus shown in FIG. 1.

FIG. 7 illustrates an exemplary image to be presented on the display section 114 in a situation where a subject, including its arterial wall, is inspected using the ultrasonic diagnostic apparatus of this preferred embodiment. As shown in FIG. 7, a tomographic image 70 representing the measuring region is presented on the display section 114. The tomographic image represents the arterial vascular lumen 41, intima 42, media 43, and adventitia 44 and the body's connective tissue 45. A region of interest 80, of which the modulus of elasticity needs to be measured, is also superimposed on the tomographic image 70. The operator can arbitrary determine the location and size of the region of interest 80 using the user interface 120 (see FIG. 2).

Also shown in the region of interest 80 are the blood flow-intima boundary 75 and the media-adventitia boundary 76 that have been located by the boundary locating section 109. The operator may determine what boundaries to show using the user interface 120.

Also, on the screen of the display section 114, the moduli of elasticity in the region of interest 80 that has been set on the tomographic image 70 are superimposed as a two-dimensional map 72. The moduli of elasticity are presented in their associated color tones or grayscales as a color bar 73. Optionally, the blood flow-intima boundary 75' and the media-adventitia boundary 76' that have been located by the boundary locating section 109 may also be shown on another tomographic image 71.

Also shown on the screen of the display section 114 is an IMT value 77 that represents the interval between the boundaries 75 and 76 on the cursor 81. The adventitia-body's connective tissue boundary 45 is not shown in FIG. 7. However, if the blood flow-intima boundary 75 and the adventitia-body's connective tissue boundary are both shown, the thickness value 78 of the vascular wall is also presented.

According to the preferred embodiment described above, at least one of the blood flow-intima boundary, the media-adventitia boundary and the adventitia-body's connective tissue boundary of the artery is located based on the information about the axial movement of the artery. That is why the thickness and IMT of the vascular wall can be obtained without producing any variation in measured value from one operator to another. In addition, the magnitude of the axial displacement is determined by making pattern matching between pieces of information about the amplitudes of the received signals. For that reason, even if some noise is superposed on the received signals, the magnitude of displacement can still be calculated accurately. As a result, the boundaries can be located accurately without being easily affected by specifications.

In the preferred embodiments described above, the ultrasonic diagnostic apparatus includes an quadrature detection section and a phase information processing section to obtain the distribution of moduli of elasticity. If there is no need to calculate the moduli of elasticity, however, those two sections may be omitted. In that case, the motion information deriving section may receive the signals from the tomographic image processing section and get the information about the axial movement of the arterial wall without providing the amplitude information processing section separately from the tomographic image processing section.

INDUSTRIAL APPLICABILITY

The present invention is effectively applicable to an ultrasonic diagnostic apparatus for use in medical applications and can be used particularly effectively to provide an ultrasonic diagnostic apparatus for inspecting the artery.

The invention claimed is:

1. An ultrasonic diagnostic apparatus comprising:
    a transmitting section configured to drive an ultrasonic probe to transmit an ultrasonic wave toward a measuring region of a subject including an arterial vascular wall;
    a receiving section configured to receive a reflected wave, produced by getting the ultrasonic wave reflected by the subject, at the ultrasonic probe to generate a received signal;
    a movement information deriving section configured to derive movement information about at least an axial movement of the arterial vascular wall based on the received signal, wherein the axial movement is movement in the direction in which the artery runs; and
    a boundary locating section configured to locate at least one of the blood flow-intima boundary, the media-adventitia boundary and the adventitia-body's connective tissue boundary of the arterial vascular wall in the measuring region based on the movement information,
    wherein the movement information comprises a radial distribution of the axial movement information at a plurality of radial positions along the radial direction of the arterial vascular wall.

2. The ultrasonic diagnostic apparatus of claim 1, further comprising a tomographic image processing section for generating a signal representing a tomographic image of the measuring region based on the received signal,
    wherein the at least one boundary is superimposed on the tomographic image.

3. The ultrasonic diagnostic apparatus of claim 2, further comprising a modulus of elasticity calculating section for calculating, based on the received signal, a modulus of elasticity between measuring points within the measuring region,
    wherein a two-dimensional map image of the moduli of elasticity calculated is further presented.

4. The ultrasonic diagnostic apparatus of claim 1, wherein the movement information comprises a displacement distribution curve representing the radial distribution, and the axial movement information comprises magnitudes of axial displacements that have been measured at the plurality of radial positions along the radial direction of the arterial vascular wall.

5. The ultrasonic diagnostic apparatus of claim 4, wherein the transmitting section and the receiving section scan the measuring region with the ultrasonic wave, thereby getting the received signals, each corresponding to one frame, a number of times, and
    wherein the movement information deriving section compares the respective amplitudes of the received signals between two different frames, thereby calculating the magnitude of axial displacement of each measuring point within the measuring region.

6. The ultrasonic diagnostic apparatus of claim 5, wherein the movement information deriving section calculates the degree of correlation between information about the amplitude of the received signal representing a first frame and information about the amplitude of the received signal representing a second frame, thereby calculating the magnitude of axial displacement of each measuring point between the two frames within the measuring region.

7. The ultrasonic diagnostic apparatus of claim 4, wherein the boundary locating section locates the blood flow-intima boundary by finding a steep rise on the displacement distribution curve that is closest to a vascular lumen.

8. The ultrasonic diagnostic apparatus of claim 4, wherein the boundary locating section locates the media-adventitia boundary by finding a local minimum value on the displacement distribution curve that is closest to the body's connective tissue.

9. The ultrasonic diagnostic apparatus of claim 4, wherein the boundary locating section locates the adventitia-body's connective tissue boundary by finding a steep fall on the displacement distribution curve that is closest to the body's connective tissue

* * * * *